(12) United States Patent
Dal Farra et al.

(10) Patent No.: US 8,349,803 B2
(45) Date of Patent: Jan. 8, 2013

(54) USE OF AN ACTIVE PRINCIPLE FROM FLAX FOR USE IN A COMPOSITION FOR ACTIVATING CYTOCHROME C

(75) Inventors: Claude Dal Farra, Opio (FR); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 283 days.

(21) Appl. No.: 12/669,836

(22) PCT Filed: Jul. 21, 2008

(86) PCT No.: PCT/FR2008/001072
§ 371 (c)(1),
(2), (4) Date: Jun. 15, 2010

(87) PCT Pub. No.: WO2009/043991
PCT Pub. Date: Apr. 9, 2009

(65) Prior Publication Data
US 2010/0279946 A1 Nov. 4, 2010

(30) Foreign Application Priority Data
Jul. 20, 2007 (FR) ..................................... 07 05295

(51) Int. Cl.
*A61K 38/00* (2006.01)
*A61P 17/00* (2006.01)

(52) U.S. Cl. ......................................... 514/18.8; 514/1.1
(58) Field of Classification Search ........................ None
See application file for complete search history.

(56) References Cited

U.S. PATENT DOCUMENTS

2003/0143288 A1* 7/2003 Mayne et al. ................. 424/725
2004/0086526 A1   5/2004 Danoux et al.

FOREIGN PATENT DOCUMENTS

| WO | 98/36748 | | 8/1998 |
| WO | 02/064129 | * | 8/2002 |
| WO | 2004/010965 | * | 2/2004 |
| WO | 2004/057976 | | 7/2004 |
| WO | 2008/015342 | | 2/2008 |

OTHER PUBLICATIONS

International Search Report dated Oct. 12, 2009, from corresponding PCT application.

* cited by examiner

*Primary Examiner* — Suzanne Ziska
(74) *Attorney, Agent, or Firm* — Young & Thompson

(57) ABSTRACT

The present invention concerns the use, in a cosmetic composition, of an effective quantity of active principle originating from flax (genus *Linum*) to activate cytochrome c and to stimulate the functions of the mitochondria. The active principle originates from the hydrolysis of flax proteins and contains principally polypeptides or peptides. It can be used alone or in association with at least one other active principle. The invention further relates to a method of cosmetic treatment intended to protect the skin and the appendages from external aggressions and to combat against cutaneous ageing.

15 Claims, No Drawings

USE OF AN ACTIVE PRINCIPLE FROM FLAX FOR USE IN A COMPOSITION FOR ACTIVATING CYTOCHROME C

The present invention lies in the cosmetic and pharmaceutical field, and more particularly in the field of dermatology. The present invention concerns the use, in a cosmetic composition, of an effective quantity of active principle originating from flax (genus *Linum*); to activate cytochrome c. Preferably, the active principle originates from the hydrolysis of flax proteins and principally contains polypeptides or peptides. It can be used alone or in association with at least one other active principle. The invention likewise relates to the use of a cosmetic composition to stimulate the functions of the mitochondria and to increase the cellular energy level. The invention further relates to a method of cosmetic treatment intended to protect the skin and the appendages from external aggressions and to combat against cutaneous ageing.

The active principle, activator of cytochrome c, can likewise be used to prepare pharmaceutical compositions intended to prevent or combat against the pathologies linked to mitochondrial dysfunctions; for example, certain neuromuscular or cardiac degenerations, type II diabetes or also certain pathologies of ageing.

The term "appendages" according to the invention encompasses all the keratinic appendages present on the surface of the body, in particular hairs, eyelashes, eyebrows, nails and head hair.

The skin is a vital organ which covers the entire surface of the body and ensures protective, sensitive, immune, metabolic or thermoregulatory functions. The skin, like the other organs, is subject to ageing. Now, one of the major mechanisms involved in the process of ageing is the accumulation of oxidative damage in essential molecules such as the membrane lipids, the proteins, the DNA and most particularly the mitochondrial DNA (mtDNA).

Oxidative damage is caused by the free radicals, chemically unstable and very reactive species generated by the intracellular metabolism or external aggressions. These external aggressions can include: UV radiation, toxins, atmospheric pollutants, alimentary oxidants.

In the skin, a premature ageing is observed, occurring in the areas exposed to radiation, characterised by phenomena of alteration to the macromolecules (lipidic peroxidation, carbonylation of proteins), affecting in particular elastin, collagen or fibronectin. A progressive decline of the mitochondrial functions with age has likewise been able to be shown, probably linked to the accumulation of mutations on mtDNA (K. Singh, Ann. N.Y. Acad. Sci. 1019, 2004).

One of the important consequences of the accumulation of oxidative damage is a reduction in the capacity of the cell to produce ATP (Porteous et al., Eur J Biochem 1998, 257(1): 192-201). Thus, the phenomenon of cellular ageing is in relation to the oxidative damage which the cell undergoes, but also to the process of energy production necessary for the cell to survive.

The organism possesses defence mechanisms capable of trapping or transforming the free radicals (enzymes, glutathione, vitamins A and E, coenzyme Q10, etc.). However, these antioxidant defence systems often prove to be insufficient with respect to the numerous stresses and external aggressions to which the organisms, and the skin in particular, are subjected.

In this context, the particular properties of cytochrome c appear as being particularly interesting:

Cytochrome c is a small soluble protein of 15 kDa which plays an essential role in mitochondrial function and in cellular survival. Cytochrome c is a highly conserved molecule in the majority of eucaryotes; it is found in the mitochondria of plants, animals and numerous unicellular organisms. Cytochrome c presents a proteic structure organised around a porphyrin, constituted by four pyrrole nuclei, themselves linked to an iron atom.

The principal role of cytochrome c is to ensure the transfer of electrons due to the change in valency of the iron atom. Cytochrome c which is soluble thus transports the electrons from complex III (coenzyme QH2 cytochrome c reductase) to complex IV (cytochrome oxydase). The electrons, which are the substrate of the cytochrome oxydase, are then transferred by the enzyme to the oxygen.

The search for compounds which are able to stimulate the mitochondria and to increase the cellular energy level so as to prevent or combat against the signs of cutaneous ageing or of damage caused by external aggressions, such as UV rays, radiations, or exposures to toxins or pollutants, is an important preoccupation in medical and cosmetics research. In this respect, solutions have been proposed such as the addition of substances involved in the energy metabolism, and more particularly of intermediaries or cofactors of the Krebs cycle, such as fumarate, L-malate, acetyl CoA (WO 02064129) or else the treatment of the skin by substances capable of reducing the free radicals, such as vitamin C (US 2004/0086526) or L-ergothioneine (WO 9836748). In addition, extracts of lignans extracted from flax have been described as beneficial for the skin (WO 2004/010965). However, to the knowledge of the applicant, no cosmetic or pharmaceutical composition has yet been described comprising compounds of peptidic nature, originating from flax, capable of activating cytochrome c.

The present invention has as its main objective the use of an effective quantity of an active principle of peptidic nature, originating from the hydrolysis of flax proteins (genus *Linum*), in a cosmetic composition to activate cytochrome c and to stimulate the mitochondria, with the aim of protecting the skin from external aggressions and of combating against cutaneous ageing. The said active principle will be able to be used alone or in association with at least one other active principle. The inventors have in fact demonstrated a biological activity, and more particularly a dermatological and cosmetic activity, of an active principle of peptidic nature originating from the hydrolysis of flax, capable of activating cytochrome c. It has been demonstrated in particular that these polypeptides or these peptides, which constitute the active principle, when they are applied on the skin, stimulate the mitochrondrial functions to a considerable extent. This has been demonstrated, inter alia, by an increase in the expression of cytochrome c, an increase in the activity of the cytochrome oxydase and an increase in the synthesis of ATP. This new active principle, which is a stimulator of the mitochondria and, more generally, is capable of protecting the skin from external aggressions, thus allows new therapeutic and cosmetic perspectives to be opened up.

"Active principle capable of protecting the skin from external aggressions" is understood to mean a hydrolysate of peptidic nature, originating from the hydrolysis of flax proteins (genus *Linum*), capable of presenting protective properties or of reducing apoptosis in cells or tissues subjected to a stress of physico-chemical or environmental origin.

"Active principle capable of activating cytochrome c" is understood to mean a hydrolysate of peptidic nature originating from the hydrolysis of flax proteins (genus *Linum*), capable of increasing the expression of cytochrome c, either by the activation of the proteic synthesis (by direct or indirect modulation of the genic expression of cytochrome c), or by the increase of the biological activity of cytochrome c, or by other biological processes such as the stabilisation of the protein cytochrome c or else the stabilisation of the messenger RNA transcripts.

"Active principle capable of stimulating the functions of the mitochondria" is understood to mean entirely a hydrolysate of peptidic nature originating from the hydrolysis of flax proteins (genus *Linum*), capable of increasing the expression or the activity of the principal active molecules present in the mitochondria, and more generally capable of increasing the principal energetic functions of the mitochondria; namely, the chain of oxidative phosphorylation and the synthesis of ATP. "Of peptidic nature" is understood to mean a mixture of compounds, represented mainly by peptides or polypeptides. The term "peptide" designates a chain of two or more amino acids linked to each other by peptidic links or by modified peptidic links; the term "polypeptide" designating a peptide of larger size.

The expression "biologically active" is understood to mean "which possesses an activity in vivo or in vitro which is characteristic of the activity of the active principle according to the invention".

The term "hydrolysate or originating from hydrolysis" designates any substance or mixture of substances, or isolated preparation, obtained after hydrolysis of vegetal manner.

The active principle according to the invention can be obtained by extraction of proteins of vegetal origin, followed by a controlled hydrolysis which releases biologically active peptidic fragments.

Numerous proteins found in plants are likely to contain biologically active peptidic fragments in the core of their structure. The managed hydrolysis allows these peptidic fragments to be released. It is possible, but not necessary to realize the invention, to extract either firstly the proteins concerned and to then hydrolyse them, or to carry out the hydrolysis first on a crude extract and to then purify the peptidic fragments. It is likewise possible to use certain hydrolysed extracts without purifying the peptidic fragments thereof corresponding to the biologically active peptides according to the invention, but nevertheless ascertaining the presence of the said fragments by suitable analytical means.

To carry out the extraction, the entire plant can be used, or a specific part of the plant (leaf, seed, etc.).

More particularly, according to the invention one of numerous plants are used of the linaceae family, of the genus *Linum* (lin). The genus *Linum* numbers almost 200 species, growing particularly in the northern hemisphere. These are herbaceous plants with fibrous stems, with simple leaves, with flowers having 5 petals. Preferably, according to the invention, the cultivated species *Linum usitatissimum* L. is used. According to the invention, the vegetal material which is used will be the seed and preferably the seed having had its envelope removed by a decortication step.

In a first stage, the plant is crushed by means of a plant crusher. The powder which is thus obtained can be subsequently "delipided" by means of a conventional organic solvent (such as for example an alcohol, hexane or acetone).

The extraction of the proteins from the plant is then carried out according to the modified conventional process (Osborne, 1924); the crushed plant material is placed in suspension in an alkaline solution containing an adsorbent product of the insoluble polyvinylpolypyrrolidone (PVPP) type (0.01-20%); in fact, it has been observed that the subsequent operations of hydrolyses and purifications were facilitated by this means. The concentration of substances of phenolic type interacting with the proteins is thus reduced.

The soluble fraction is collected after centrifugation and filtration stages, this crude solution therefore constituting a first form of the extract containing the proteins, the carbohydrates and possibly lipids.

The proteins are then precipitated, varying the ionic force by acidifying the medium, which allow the soluble components and the nucleic acids to be eliminated.

The precipitate is then washed by means of an organic solvent such as, for example, ethanol or methanol, then the solvent is evaporated by drying under vacuum. The precipitate, which is rich in proteins, is returned to solution in water or another solvent, and therefore constitutes a more purified form of the hydrolysate.

The extraction can likewise be realized in neutral or acid medium, still in the presence of polyvinylpolypyrrolidone. After a filtration stage, the precipitation stage is then carried out by means of a conventional precipitation agent such as salts (sodium chloride, ammonium sulphate) or an organic solvent (alcohol, acetone). The precipitate which is obtained can be separated from the precipitation agents by dialysis after returning to solution in water or another solvent.

The isolated proteic fraction according to the invention is then hydrolysed in conditions arranged to generate soluble peptides and polypeptides. Hydrolysis is defined as being a chemical reaction involving the cleavage of a molecule by water, this reaction being able to be carried out in neutral, acid or basic medium. According to the invention, the hydrolysis is realized chemically and/or advantageously by proteolytic enzymes. The use can therefore be cited of endoproteases of vegetal origin (papain, bromelaine, ficin) and micro-organisms (Aspergillus, Rhizopus, Bacillus, etc.).

For the same reasons as previously, in this managed hydrolysis stage, a quantity of polyvinylpolypyrrolidone is added to the reaction medium. After filtration, the solution which is obtained constitutes the active hydrolysate. The active hydrolysate can be further purified so as to select the molecular weights and the nature of the generated peptides. The fractionation can be carried out advantageously by ultrafiltration and/or by a method of the chromatographic type.

Any of the more or less purified forms of the hydrolysate is then solubilised in water or in any mixture containing water, then sterilised by ultrafiltration.

The vegetal hydrolysate obtained according to the invention is analysed qualitatively and quantitatively for its physico-chemical characteristics and its content of compounds of proteic and peptidic nature. Compounds of peptidic nature are understood to mean the fragments of proteins, the peptides and the free amino acids present in the mixture. The peptides, amino acids and fragments of proteins are dosed according to conventional techniques which are well known to the man skilled in the art.

Thus, according to an advantageous embodiment of the invention, the active vegetal hydrolysate has a pH comprised between 4 and 7, and preferably between 5 and 6, a dry extract titrating between 1 and 8 g/l, and preferably between 2 and 5 g/l, its content of compounds of peptidic nature is comprised between 0.1 and 5 g/l, and preferably between 0.5 and 2 g/l and its content of sugars is from 0.5 to 2.5 g/l.

According to an advantageous embodiment of the invention, the active principle according to the invention is previously solubilised in one or more cosmetically or pharmaceutically acceptable solvents, conventionally used by the man skilled in the art, such as water, glycerol, ethanol, propylene glycol, butylene glycol, dipropylene glycol, ethoxylated or propoxylated diglycols, cyclic polyols, petroleum jelly, a vegetal oil or any mixture of these solvents.

According to another further advantageous embodiment of the invention, the active principle according to the invention is previously solubilised in a cosmetic or pharmaceutical vector such as liposomes, or adsorbed on powdery organic polymers, mineral supports such as talcs and bentonites, and more generally solubilised in, or fixed on, any cosmetically or pharmaceutically acceptable vector.

The composition which is able to be used according to the invention can consist in particular of a composition for capillary care, and in particular a shampoo, a conditioner, a setting lotion, a treatment lotion, a hairdressing cream or gel, a restructuring lotion for the hair, a mask, etc. The cosmetic composition according to the invention can be used in particular in treatments implementing an application which is followed, or not followed, by a rinsing, or else in the form of a shampoo.

It can likewise present itself in the form of a dye or mascara to be applied by a brush or by a comb, in particular on the eyelashes, the eyebrows or the hair.

It is readily understood that the active principle according to the invention can be used alone or else in association with at least one other active principle, in a cosmetic composition or for the preparation of a pharmaceutical and/or dermatological composition.

The compositions according to the invention will be able to be applied by any suitable manner, in particular orally, parenterally or externally topically, and their formulation will be adapted by the man skilled in the art, in particular for cosmetic or dermatological compositions. Advantageously, the compositions according to the invention are intended for an administration in a topical cutaneous manner. These compositions must therefore contain a cosmetically and/or dermatologically acceptable medium, i.e. compatible with the skin and the appendages, and cover all the cosmetic or dermatological forms. In particular, these compositions will be able to be in the form of creams, oil-in-water emulsions, or water-in-oil or multiple emulsions, solutions, suspensions, gels, milks, lotions, sticks or else powders, suited to an application on the skin, the lips and/or the appendages.

These compositions comprise the necessary excipients for their formulation, such as solvents, thickeners, thinners, surfactants, antioxidants, colouring agents, preservatives, perfumes.

Advantageously, the compositions which are able to be used according to the invention further contain other active principles intended to promote its action. Among these other active principles, the active principles can be named which have an anti-radical or antioxidant action, selected from vitamin C, vitamin E, the coenzyme Q10 and polyphenolic plant extracts.

"Anti-radical active principles" are understood to mean any compound capable of trapping the free radicals. These active principles are capable of blocking the chain reactions of the free radicals before the final degradation stages of the biological constituents of the skin and thus have an antioxidant activity. Among these other active principles, one can likewise name the active principles stimulating the syntheses of the dermic macromolecules (laminin, fibronectin, collagen), for example collagen peptide sold under the name "Collaxyl®" by the company Vincience.

Among these other active principles, one can finally name the active principles stimulating the energetic metabolism, like the active principle sold under the name "GP4G®" by the company Vincience.

According to another aspect, the composition according to the invention can be a sun composition, i.e. a composition assisting in the protection against solar radiation. Thus, actives assisting in solar protection, such as for example, solar filters, can be advantageously added to the composition according to the invention.

It is readily evident that the invention is addressed to mammals in general and more particularly to human beings.

The effective quantity of active principle corresponds to the quantity necessary so as to obtain the result which is sought, namely: to activate the cytochrome c, to stimulate the mitochondria and to increase the cellular energy level, and more generally to protect the skin and the appendages from external aggressions and to combat against cutaneous ageing.

According to an advantageous embodiment of the invention, the active principle is present in the compositions of the invention at a concentration comprised between 0.0001% to 20% approximately, and preferably at a concentration comprised between 0.05% and 5% approximately with respect to the total weight of the final composition.

These compositions will be able to present themselves, in particular, in the form of an aqueous, hydroalcoholic or oily solution; an oil-in-water, water-in-oil emulsion or multiple emulsions; they can also present themselves in the form of creams, suspensions, or else powders, suited to an application on the skin, the mucosa, the lips and/or the appendages. These compositions can be more or less fluid and can have the appearance of a cream, a lotion, a milk, a serum, an ointment, a gel, a paste or a foam. They can also present themselves in solid form, as a stick or can be applied on the skin in the form of an aerosol. They can be used as a care product and/or as a make-up product for the skin.

These compositions further comprise any additive commonly used in the envisaged field of application and also the adjuvants necessary for their formulation, such as solvents, thickeners, thinners, antioxidants, colouring agents, solar filters, suntan simulating agents, pigments, charges, preservatives, perfumes, odour absorbers, cosmetic or pharmaceutical actives, essential oils, vitamins, essential fatty acids, surfactants, film-forming polymers, etc.

In all cases, the man skilled in the art will ensure that the adjuvants and their proportions are selected in such a way as to not be prejudicial to the sought advantageous properties of the composition according to the invention. These adjuvants can, for example, correspond to 0.01 to 20% of the total weight of the composition. When the composition of the invention is an emulsion, the fatty phase can represent from 5 to 80% by weight and preferably from 5 to 50% by weight with respect to the total weight of the composition. The emulsifiers and co-emulsifiers used in the composition will be selected from those conventionally used in the field concerned. For example, they can be used in a proportion from 0.3 to 30% by weight, with respect to the total weight of the composition.

By its particular activities, the active principle according to the invention will be able to be used advantageously in a cosmetic composition or for the preparation of a pharmaceutical composition.

In particular, the active principle according to the invention will be able to be used advantageously in a cosmetic preparation intended to combat in a preventive and/or curative manner against the manifestations of cutaneous ageing and, more specifically, so as to combat against and/or to prevent photo-induced ageing (photo-ageing). Cutaneous manifestations of ageing are understood to mean all modifications of the exterior appearance of the skin and the appendages due to ageing, such as, for example, wrinkles and fine lines, withered skin, flabby skin, thinned skin, the lack of elasticity and/or of tonus of the skin, dull skin without brightness, or pigmentation blemishes of the skin, discolouration of the hair or blemishes on the nails, but likewise any internal modification of the skin which is not ultimately resulting systematically in a modified exterior appearance, such as for example any internal degradation of the skin following an exposure to ultraviolet radiation (UV). The active principle according to the invention, or the composition containing it, will allow one to combat, in particular, against the loss of elasticity and of firmness of the skin.

The active principle according to the invention allows the skin and the appendages to be protected against all types of external aggressions. The use of the active principle, or of a composition containing it, will allow the skin and the appendages to be protected and to better resist environmental stresses.

The expression "external aggression" is understood to mean the aggressions which can be produced by the environment. By way of example, one can name aggressions such as pollution, UV rays, or else products of an irritant character such as surfactants, preservatives or perfumes. Pollution is understood to mean both "external" pollution, due for example to diesel particles, ozone or heavy metals, and "interior" pollution which can be due in particular to the emissions of solvents of paints, glues or wallpapers (such as toluene, styrene, xylene or benzaldehyde), or else cigarette smoke.

The active principle according to the invention can be advantageously used in a cosmetic composition or for the preparation of a pharmaceutical composition, as a photo-protective agent and, more particularly, as a photo-protective agent which is designated "secondary". A distinction is in fact made between primary photo-protective agents and secondary photo-protective agents. The primary photo-protective agents are substances which exert a physical power: they are able to absorb UV radiation and to restore it in the form of heat so as to protect the skin. The secondary photo-protective agents are substances which generally have a biological effect; they are, for example, agents capable of limiting the damage caused to the DNA and to the membranes by the penetration of UV radiation on the skin.

The invention further relates to use in a cosmetic composition, or for the preparation of a pharmaceutical composition, of an effective quantity of active principle according to the invention, the active principle or the composition containing it, being intended to increase the intracellular ATP synthesis of the cells of the skin.

The invention likewise has as an object the use in a cosmetic composition, or for the preparation of a pharmaceutical composition, of an effective quantity of active principle according to the invention, the active principle, or the composition containing it, being intended to prevent damage caused to the skin by an exposure to the sun or an exposure to ionising radiation during radiotherapies.

The invention likewise has as an object the use in a cosmetic composition, or for the preparation of a pharmaceutical composition, of an effective quantity of active principle according to the invention, the active principle, or the composition containing it, being intended to stimulate the mitochondria, in particular on the areas of the body which are exposed to UV radiation.

The invention further relates to the use in a cosmetic composition, or for the preparation of a pharmaceutical composition, of an effective quantity of active principle as previously described, the active principle, or the composition containing it, being intended to protect the skin from damage caused by free radicals.

The invention further consists in the use of an effective quantity of active principle to prepare a pharmaceutical composition intended to prevent or to combat against certain pathologies linked to mitochondrial dysfunctions, for example certain neuromuscular or cardiac degenerations, type II diabetes, certain pathologies of ageing.

The invention further consists of a method of cosmetic treatment intended to stimulate the defences and to protect the skin and the appendages from external aggressions and to combat against cutaneous ageing, characterized by the application on the skin or the appendages which are to be treated of a composition containing an effective quantity of active principle according to the invention.

The invention further consists of a method of cosmetic treatment intended to give a healthier appearance to the skin and to improve the brightness and radiance of the complexion, characterized by the application on the skin which is to be treated of a composition containing an effective quantity of active principle according to the invention.

Particular embodiments of this method of cosmetic treatment likewise result from the preceding description. Other advantages and characteristics of the invention will be better apparent from reading examples, given by way of illustration and not restrictively.

EXAMPLE 1

Preparation of Active Principle from Flax (*Linum usitatissimum* L.)

The active principle is obtained from plants of the species *Linum usitatissimum* L. Of course, the extract can be prepared from plants from at least any one of the numerous varieties and species belonging to the genus *Linum*.

In a first stage, 1 kg of decorticated flax seeds are crushed in a cereal crusher. The flour which is obtained is delipided by the action of an organic solvent, hexane. After filtration and drying under vacuum, the powder which is obtained is placed in suspension in an alkaline aqueous solution (dilution at $\frac{1}{10}$) pH 10 containing 1% of polyvinylpolypyrrolidone (Polyclar V ISP). This mixture is kept under stirring for a sufficiently long time to allow the solubilisation of the soluble fractions. The extraction temperature is variable (comprised between 4 and 80° C.); preferably the operation will be carried out cold. After this extraction phase, the medium is clarified by centrifuging, then filtered on a plate filter. This filtrate which contains the soluble fractions of the flax is then subjected to a precipitation of the proteins, varying the ionic force in neutral or acid medium, which allows the soluble glucidic components to be eliminated, the lipids and the nucleic acids, the medium is brought to pH 3.5. The supernatant is eliminated and the precipitate is then washed by means of a solvent such as, for example, ethanol or methanol then the solvent is evaporated by drying under vacuum.

At this stage, one obtains approximately 50 grams of powder of light yellow colour of crude bruteic extract containing
  Proteins: 75%
  Carbohydrates: 20%
  Lipids: 5%
The precipitate, rich in proteins, is returned to solution in water or another solvent.

The crude proteic extract is then subjected to a series of managed and selective hydrolyses consisting of chemical and enzymatic hydrolyses in the presence of 0.5% of PVPP (Polyclar V) and of cysteine endopeptidases (papain, ficin). After reaction, the hydrolysate is filtered on a plate then on sterilising cartridge (0.2 µm).

A light-coloured hydrolysate is then obtained, titrating from 15 to 30 g/l of dry extract, which is then diluted such that the concentration of compounds of peptidic nature determined by the Lowry method, is comprised between 0.1 and 5 g/l and preferably between 0.5 and 2 g/l. The physico-chemical analysis of the vegetal hydrolysate, which constitutes the active principle, shows that its pH is comprised between 4 and 7, and preferably between 5 and 6, the dry extract titrates from 1 to 8 g/l and preferably between 2 and 5 g/l, its content of compounds of peptidic nature is comprised between 0.1 and 5 g/l, and preferably between 0.5 to 2 g/l and its content of sugars between 0.5 to 2.5 g/l.

EXAMPLE 2

Preparation of Active Principle from Flax (*Linum usitatissimum* L.)

A variant of the protocol of Example 1 consists in carrying out the same sequence of managed and selective enzymatic hydrolyses, but in the presence of 0.5% of PVPP.

One then obtains a light-coloured hydrolysate titrating from 15 to 30 g/l of dry extract after sterilising filtration.

One then proceeds to an ultrafiltration of the solution on a Millipore Helicon filtration cartridge (cutoff threshold; 1 kDa). The high molecular weights contained in the retentate are eliminated, the filtrate is retained.

The concentration of compounds of peptidic nature is determined by the Lowry method, either comprised between 0.1 and 5 g/l and preferably between 0.5 and 2 g/l. The physico-chemical analysis of the vegetal hydrolysate, which constitutes the active principle, shows that its pH is comprised between 4 and 7, and preferably between 5 and 6, the dry extract titrates between 1 to 8 g/l, and preferably between 2 and 5 g/l, its content of compounds of peptidic nature is comprised between 0.1 and 5 g/l and preferably between 0.5 to 2 g/l and its content of sugars between 0.5 to 2.5 g/l.

Another variant consists in carrying out a purification of the active principle, obtained according to Example 1 or 2, by ion exchange chromatography, on a gel TSK column (Toso-Haas) with a pH7 phosphate buffer.

EXAMPLE 3

Demonstration of the Stimulating Effect of the Active Principle According to Example 1 on the Synthesis of Intracellular ATP The aim of this study is to determine the influence of the active principle according to Example 1 on the synthesis of ATP, produced by the mitochondria.

Protocol: This study is carried out by means of a kit "ATP Bioluminescence Assay Kit HS II" (Roche Applied Science). Dermal fibroblasts are treated with a 1% solution of active principle according to Example 1, for a period of from 1 to 3 hours. At the end of the incubation, the wells are rinsed with 2 ml of cold PBS before adding 250 µl of a lysis buffer provided by the kit. The cells of each well are then scraped, then collected in 14 ml tubes. Each well is rinsed with 2×500 µl cold PBS and the whole is collected again in the respective tubes. From these samples, a dilution is carried out at $\frac{1}{12000}^{th}$ in cold PBS before each reading. The ATP dosage is carried out on these samples: 50 µL of this dilution are deposited in a luma cuvette and 50 µL of luminol are added. After 10 seconds, the reading of the luminescence is started. The values are standardised with respect to the quantity of proteins for each sample. The measurements are carried out by means of an apparatus: the Biocounter M2010A LUMAC®/3M.

Results: The dosages of ATP show that there is a great increase in the quantity of intracellular ATP after 1 hour and 3 hours, in cells treated by the active principle according to Example 1, in comparison with the non-treated cells.

Conclusion: The active principle according to Example 1 increases appreciably the energetic level of cutaneous cells such as fibroblasts, and more generally stimulates the mitochondrial functions.

EXAMPLE 4

Demonstration of the Activating Effect of the Active Principle According to Example 1 on the Expression of Cytochrome c The aim of this study is to determine the influence of the active principle according to Example 1 on the expression of cytochrome c. For this, the quantity of cytochrome c was evaluated by the technique of immuno-transfer (or Western blot).

Protocol: Human dermal fibroblasts are treated with a 1% solution of active principle according to Example 1, for 72 hours. The cells are then lysed and homogenised by sonication, then centrifuged for 10 minutes at 1000 g. The samples, which are standardised for their protein concentration (dosage kit BCA, Pierce), are subjected to an electrophoresis on gel Bis-TRIS 4-12% (InvitroGen). After electro-transfer, the membranes are incubated for one night with an anti-cytochrome c antibody, diluted at $\frac{1}{500}$ (Mouse monoclonal anti cytochrome c, TEBU). A secondary antibody, coupled to peroxydase and diluted at $\frac{1}{5000}$ is then used (peroxydase conjugated F(ab')$_2$, Goat antimouse, Immunotech). The chemiluminescent signal is then quantified with the aid of the kit Supersignal West Femto Trial kit and read in a reading chamber (Multilmage light Cabinet, Alpha Immunotech Corporation).

Results: A clear increase is observed of the expression of cytochrome c in the fibroblasts treated by the active principle according to Example 1.

Conclusions: The active principle according to Example 1 greatly stimulates the expression of cytochrome c in the cutaneous cells, and more generally the mitochondrial functions.

EXAMPLE 5

Demonstration of the Activating Effect of the Active Principle According to Example 1 on the Enzymatic Activity of the Cytochrome Oxydase The aim of this study is to determine the influence of the active principle according to Example 1 on the mitochondrial activity. For this, the total enzymatic (mitochondrial) activity of the cytochrome oxydase was measured.

Protocol: Normal human fibroblasts are treated with a 1% solution of active principle according to Example 1 for 3 hours and 24 hours. The cells are collected, rinsed, then lysed by sonication. A first centrifuging is carried out to eliminate the principal cellular debris and the supernatant is then centrifuged again at 10 000 g for 10 min. The enzymatic activity is dosed in the supernatant and/or in the $2^{nd}$ cell pellet by a biochemical method, with the aid of the kit Cytocox 1 (Sigma), then standardised for the content of proteins (dosed by the kit PCA, Pierce).

Results: The dosages show that there is a very great increase in the enzymatic activity of the cytochrome oxydase after 3 hours and 24 hours of application of the active principle according to Example 1, in comparison with the non-treated cells.

Conclusion: The active principle according to Example 1 stimulates very greatly the enzymatic activity of the cytochrome oxydase, and more generally the mitochondrial activity, in the cutaneous cells.

EXAMPLE 6

Demonstration of the Protective Effect of the Active Principle According to Example 1 on the Mitochondrial Membrane Potential The aim of this study is to determine the protective effect of the active principle according to Example 1, with respect to mitochondria of dermal fibroblasts subjected to an oxidative stress, caused by oxygenated water ($H_2O_2$) or a UVB irradiation. For this, one uses a marker of the membrane potential of the mitochondria (JC-1). JC-1 is a marker which emits a different fluorescence according to the level of polarisation of the mitochondrial membrane.

Protocol: The human dermal fibroblasts are treated with a 1% solution of active principle according to Example 1 for 96 hours, then subjected to an oxidative stress caused by $H_2O_2$ at 2 mM for 30 minutes, or to an irradiation by UVB at 50 mJ/cm$^2$. Controls which are not treated by the peptide or by $H_2O_2$ or are not irradiated are realized under the same conditions. At the end of the experiment, the cells are washed, fixed and subjected to a marking by a solution of JC-1 (Molecular Probes) at 0.2 µg/ml, so as to reveal the membrane potential of the mitochondria.

Results: In the fibroblasts treated by the active principle according to Example 1, the mitochondria present a red fluorescence (JC-1 aggregate), the sign of a high membrane potential, greater than in the control cells. The fibroblasts which were irradiated or subjected to an oxidative stress have mitochondria which fluoresce little in the red range, and principally in the green range (monomeric JC-1), the sign of an alteration of the mitochondrial membrane potential. Under these latter conditions, the application of the active principle according to Example 1 allows a more marked red fluorescence to be observed.

Conclusions: The application of the active principle according to Example 1 causes an increase in the membrane potential of the mitochondria. Moreover, the active principle according to Example 1 efficiently protects the mitochondria of the cutaneous cells subjected to an oxidative stress or to an irradiation by UVB.

EXAMPLE 7

Preparation of Compositions

1—Sun Protection Cream:

| Commercial names | INCI names | % mass |
|---|---|---|
| PHASE A | | |
| Demineralised water | Aqua (Water) | qs |
| Pemulen TR1 | Acrylates/C10-30 Alkyl Acrylate Crosspolymer | 0.40 |
| Glycerine | Glycerin | 3.00 |
| Nipastat Sodium | Sodium Methylparaben (and) Sodium Ethylparaben (and) Sodium Butyl paraben (and) Sodium Propylparaben (and) Sodium Isobutylparaben | 0.15 |
| PHASE B | | |
| Parsol MCX | Ethylhexyl Methoxycinnamate | 7.50 |
| Eusolex 4360 | Benzophenone-3 | 3.00 |
| Parsol 1789 | Butyl Methoxydibenzoylmethane | 2.00 |
| Myritol 318 | Caprylic/Capric Triglyceride | 4.00 |
| Emulgade SEV | Hydrogenated Palm Glycerides (and) Ceteareth-20 (and) Ceteareth-12 (and) Cetearyl Alcohol | 5.00 |
| Propylparaben | Propylparaben | 0.15 |
| Nacol 16-98 | Cetyl Alcohol | 1.00 |
| PHASE C | | |
| TEA | Triethanolamine | 0.20 |
| PHASE D | | |
| Active principle of Example 1 | | 3 |
| Perfume | Parfum (Fragrance) | qs |
| Colouring agent | | qs |

The constituents of Phase A and Phase B are heated separately between 70° C. and 75° C. Phase B is emulsified in Phase A under stirring. Phase C is added, at 45° C., increasing the stirring. Phase D is then added when the temperature is below 40° C. The cooling is continued to 25° C. under strong stirring.

2—After-Sun Milk:

| Commercial names | INCI names | % mass |
|---|---|---|
| PHASE A | | |
| Montanov L | C14-22 Alcohols (and) C12-20 Alkyl Glucoside | 3.00 |
| Waglinol 2559 | Cetearyl Isononanoate | 4.00 |
| Tegosoft TN | C12-15 Alkyl Benzoate | 3.00 |
| Apricot kernel oil | Prunus Armeniaca (Apricot) Kernel Oil | 2.00 |
| Avocado oil | Persea Gratissima (Avocado) Oil | 1.00 |
| Abil 350 | Dimethicone | 1.00 |
| PHASE B | | |
| Demineralised water | Aqua (Water) | qs |
| PHASE C | | |
| Simulgel EG | Sodium Acrylate/Acryloyldimethyl Taurate Copolymer (and) Isohexadecane (and) Polysorbate 80 Copolymer (and) Polysorbate 80 | 0.4 |
| PHASE D | | |
| Phenonip | Phenoxyethanol (and) Methylparaben (and) Ethylparaben (and) Butylparaben (and) Propylparaben (and) Isobutylparaben Ethylparaben and Propylparaben and Buthylparaben | 0.30 |
| Germall 115 | Imidazolidinyl Urea | 0.20 |
| PHASE E | | |
| Active principle of Example 1 | | 0.1 |

Prepare Phase A under stirring. Incorporate the xanthan gum progressively, under deflocculating stirring. Phases C and D will be incorporated once the gel is finished. Phase E, prepared previously up to perfect dissolving of the DHA, will then be added. Adjust the pH if necessary to 4-4.5. Colour and perfume.

3—Anti-Ageing Cream:

| Commercial names | INCI names | % mass |
|---|---|---|
| Phase A | | |
| Montanov 68 | Cetearyl Alcohol (and) Cetearyl Glucoside | 6.00 |
| Squalane | Squalane | 3.00 |
| Cetiol SB 45 | Butyrospermum Parkii (Shea Butter) | 2.00 |
| Waglinol 250 | Cetearyl Ethylhexanoate | 3.00 |
| Amerchol L-101 | Mineral Oil (and) Lanolin Alcohol | 2.00 |
| Abil 350 | Dimethicone | 1.50 |
| BHT | BHT | 0.01 |
| Coenzyme Q10 | Ubiquinone | 0.10 |
| Phase B | | |
| Avocado oil | Persea Gratissima (Avocado) Oil | 1.25 |
| Phenonip | Phenoxyethanol (and) Methylparaben (and) Ethylparaben (and) Butylparaben (and) Propylparaben (and) Isobutylparaben | 0.75 |
| Phase C | | |
| Demineralised water | Aqua (Water) | qs |
| Butylene Glycol | Butylene Glycol | 2.00 |
| Glucam E10 | Methyl Gluceth-10 | 1.00 |
| Allantoin | Allantoin | 0.15 |
| Carbopol Ultrez 10 | Carbomer | 0.20 |
| Phase D | | |
| TEA | Triethanolamine | 0.18 |
| Phase E | | |
| Active principle of Example 1 | | 0.5 |
| GP4G | Water (and) Artemia Extract | 1.50 |
| Collaxyl | Water (and) Butylene Glycol (and) Hexapeptide-9 | 3.00 |
| Phase F | | |
| Perfume | Parfum (Fragrance) | qs |
| Colouring agent | | qs |

Prepare and melt Phase A at 65-70° C. Heat Phase C at 65-70° C. Phase B is added to Phase A just before emulsifying A in B. At approximately 45° C., the carbomer is neutralised by addition of Phase D. Phase E is then added under light stirring and the cooling is continued to 25° C. Phase F is then added, if desired.

4—Protective Day Cream:

| Commercial names | INCI names | % mass |
|---|---|---|
| Phase A | | |
| Emulium Delta | Cetyl alcohol (and) Glyceryl Stearate (and) PEG-75 Stearate (and) Ceteth-20 (and) Steareth-20 | 4.00 |
| Lanette O | Cetearyl Alcohol | 1.50 |
| D C 200 Fluid/100 cs | Dimethicone | 1.00 |
| DUB 810C | Coco Caprylate/Caprate | 1.00 |
| DPPG | Propylene Glycol Dipelargonate | 3.00 |
| DUB DPHCC | Dipentaerythrityl Hexacaprylate/Hexacaprate | 1.50 |
| Cegesoft PS6 | Vegetable Oil | 1.00 |
| Vitamin E | Tocopherol | 0.30 |
| Phenonip | Phenoxyethanol (and) Methylparaben (and) Ethylparaben (and) Butylparaben (and) Propylparaben (and) Isobutylparaben | 0.70 |
| Phase B | | |
| Demineralised water | Aqua | qsp 100 |
| Glycerine | Glycerin | 2.00 |
| Carbopol EDT 2020 | Acrylates/C10-30 Alkyl Acrylate Crosspolymer | 0.15 |
| Keltrol BT | Xanthan Gum | 0.30 |
| Phase C | | |
| Sodium Hydroxide (sol. 10%) | Sodium Hydroxide | 0.30 |
| Phase D | | |
| Demineralised water | Aqua | 5.00 |
| Stay-C 50 | Sodium Ascorbyl Phosphate | 0.50 |
| Phase E | | |
| Butylene Glycol | Butylene Glycol | 2.00 |
| Dekaben CP | Chlorphenesin | 0.20 |
| Phase F | | |
| GP4G | Water (and) Artemia Extract | 1.00 |
| Active principle of Example 1 | | 5 |

Prepare Phase A and heat at 75° C. under stirring. Prepare Phase B, dispersing the carbopol, then the xanthan gum under stirring. Allow to rest. Heat at 75° C.

At temperature, emulsify A in B under rotor-stator stirring. Neutralise with Phase C under rapid stirring. After cooling at 40° C., add Phase D, then Phase E. The cooling is continued under light stirring and Phase F is added.

The invention claimed is:

1. A flax seed hydrolysate (genus *Linum*) consisting of chemical and enzymatic hydrolyses in the presence of polyvinylpolypyrrolidone in an aqueous alkaline solution and of cysteine endopeptidases, wherein the hydrolysate is an active principle of peptidic nature, having a pH comprised between 4 and 7, a dry extract titrated between 1 and 8 g/l, a content of compounds of peptidic nature comprised between 0.1 and 5 g/l, and a content of sugars comprised between 0.5 and 2.5 g/l.

2. The flax seed hydrolysate according to claim 1, wherein, said active principle originates from flax seeds of the species *Linum usitatissimum* L.

3. The flax seed hydrolysate (genus *Linum*) according to claim 1, wherein said active principle is previously solubilised in one or more cosmetically or pharmaceutically acceptable solvents selected from the group consisting of water, glycerol, ethanol, propylene glycol, butylene glycol, dipropylene glycol, ethoxylated or propoxylated diglycols, cyclic polyols, petroleum jelly, a vegetal oil and mixtures thereof.

4. A cosmetic composition comprising a flax seed hydrolysate (genus *Linum*) according to claim 1 as an active principle in a cosmetically or dermatologically acceptable medium.

5. The composition according to claim 4 wherein the active principle is from 0.0001% to 20% of the total weight of the composition.

6. The composition according to claim 5, wherein the active principle is from 0.05% to 5% of the total weight of the composition.

7. The composition according to claim 4, wherein the said composition is in a form for topical application.

8. The composition according to claim 4, further comprising at least one other active principle promoting the action of the flax seed hydrolysate.

9. The composition according to claim 8, wherein the at least one other active principle is selected from the group consisting of an antioxidant active principle, an active principle stimulating the synthesis of the extracellular matrix, an active principle stimulating the energetic cellular metabolism and mixtures thereof.

10. A method of preparing a cosmetic composition activating cytochrome c, stimulating the mitochondria and increasing the synthesis of intracellular ATP of the cells of the skin, comprising:

adding an effective quantity of an active principle of peptidic nature obtained from chemical and enzymatic hydrolyses in the presence of polyvinylpolypyrrolidone in an aqueous alkaline solution and of cysteine endopeptidases of flax proteins (genus *Linum*) in a cosmetically or dermatologically acceptable medium.

11. A method of activating cytochrome c, stimulating the mitochondria and increasing the synthesis of intracellular ATP of the cells of the skin, comprising:

topically applying an effective quantity of an active principle of peptidic nature, wherein, said active principle is in a cosmetic composition, and said active principle is obtained from chemical and enzymatic hydrolyses in the presence of polyvinylpolypyrrolidone in an aqueous alkaline solution and of cysteine endopeptidases of flax proteins (genus *Linum*).

12. The method according to claim 11, wherein, said cosmetic composition is intended to protect the skin and the appendages against all types of external aggression.

13. The method according to claim 12, wherein, said external aggressions are UV radiations.

14. The method according to claim 11, wherein, said cosmetic composition is intended to prevent or to treat the cutaneous signs of ageing and/or of photo-ageing.

15. The method according to claim 11, wherein, said cosmetic composition is intended to improve the brightness and the radiance of the complexion.

* * * * *